US012788221B2

(12) United States Patent
Fu et al.

(10) Patent No.: US 12,788,221 B2
(45) Date of Patent: Nov. 10, 2026

(54) POSITIONING AID, POSITIONING AID SYSTEM FOR ENDOSCOPE AND GUIDE SHEATH, AND METHOD FOR ATTACHING GUIDE SHEATH

(71) Applicant: OLYMPUS CORPORATION, Tokyo (JP)

(72) Inventors: Yuchun Fu, Tokyo (JP); Chisato Kikuchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 577 days.

(21) Appl. No.: 18/165,716

(22) Filed: Feb. 7, 2023

(65) Prior Publication Data

US 2023/0181012 A1 Jun. 15, 2023

Related U.S. Application Data

(63) Continuation of application No. PCT/JP2020/032158, filed on Aug. 26, 2020.

(51) Int. Cl.
*A61B 1/00* (2006.01)

(52) U.S. Cl.
CPC ................................ *A61B 1/00154* (2013.01)

(58) Field of Classification Search
CPC ............ A61B 1/00154; A61B 1/00135; A61B 1/0008; A61B 1/00101; A61B 1/00105; A61B 1/0011
See application file for complete search history.

(56) References Cited

U.S. PATENT DOCUMENTS

| | | | | |
|---|---|---|---|---|
| 5,386,817 | A * | 2/1995 | Jones | A61B 1/00135 600/125 |
| 5,685,822 | A | 11/1997 | Harhen | |
| 8,545,394 | B2 | 10/2013 | Motai et al. | |
| 8,979,884 | B2 | 3/2015 | Milsom et al. | |
| 9,924,853 | B2 | 3/2018 | Milsom et al. | |
| 9,986,893 | B2 | 6/2018 | Cornhill et al. | |
| 10,149,601 | B2 | 12/2018 | Cornhill et al. | |
| 10,485,401 | B2 | 11/2019 | Cruz et al. | |

(Continued)

FOREIGN PATENT DOCUMENTS

| | | | |
|---|---|---|---|
| CN | 111419147 | A | 7/2020 |
| CN | 306393316 | A | 3/2021 |

(Continued)

OTHER PUBLICATIONS

"International Application Serial No. PCT/JP2020/032158, International Search Report dated Oct. 20, 2020", (Oct. 20, 2020), 5 pgs.

*Primary Examiner* — Timothy J Neal
(74) *Attorney, Agent, or Firm* — Schwegman Lundberg & Woessner. P.A.

(57) ABSTRACT

A positioning aid includes an opening configured to be inserted a distal end portion of an endoscope; and an alignment portion configured to be aligned with a particular alignment subject on a distal end surface of the endoscope. The alignment portion is configured to line up with the particular alignment subject in a longitudinal direction of the endoscope in a state where the endoscope inserted into the opening and a guide sheath are arranged to have a particular positional relationship in a circumferential direction about a longitudinal axis of the endoscope.

15 Claims, 15 Drawing Sheets

(56) References Cited

U.S. PATENT DOCUMENTS

| | | | | |
|---|---|---|---|---|
| 2005/0043584 | A1* | 2/2005 | Nozue ................ | A61B 1/00089 600/127 |
| 2020/0146530 | A1 | 5/2020 | Cruz et al. | |

FOREIGN PATENT DOCUMENTS

| | | | |
|---|---|---|---|
| JP | 2009089725 | A | 4/2009 |
| WO | WO-2009044605 | A1 | 4/2009 |
| WO | WO-2010082399 | A1 | 7/2010 |

* cited by examiner

POSITIONING AID, POSITIONING AID SYSTEM FOR ENDOSCOPE AND GUIDE SHEATH, AND METHOD FOR ATTACHING GUIDE SHEATH

CLAIM OF PRIORITY

This is a continuation of International Application PCT/JP2020/032158 which is hereby incorporated by reference herein in its entirety

TECHNICAL FIELD

The present invention relates to a positioning aid, a positioning aid system for an endoscope and a guide sheath, and a method for attaching a guide sheath.

BACKGROUND ART

Conventionally, there is a known guide sheath that is attached to the exterior of an endoscope and has two treatment tool channels (for example, see PTL 1). Treatment tools such as forceps and a surgical knife can be inserted into the body along with an endoscope by using such a guide sheath.

CITATION LIST

Patent Literature

{PTL 1}
U.S. Pat. No. 10,485,401

SUMMARY OF INVENTION

An aspect of the present invention provides a positioning aid configured to help positioning a guide sheath relative to an endoscope, the positioning aid including: an opening configured to be inserted a distal end portion of an endoscope; and an alignment portion configured to be aligned with a particular alignment subject on a distal end surface of the endoscope, wherein the alignment portion is configured to line up with the particular alignment subject in a longitudinal direction of the endoscope in a state where the endoscope inserted into the opening and a guide sheath are arranged to have a particular positional relationship in a circumferential direction about a longitudinal axis of the endoscope.

Another aspect of the present invention provides a positioning aid system including: a guide sheath into which an endoscope is to be inserted; and a positioning aid configured to be attached to the guide sheath, wherein the positioning aid is configured to help positioning the guide sheath relative to the endoscope, wherein the positioning aid includes: an opening configured to be inserted a distal end portion of the endoscope; and an alignment portion configured to be aligned with a particular alignment subject on a distal end surface of the endoscope, wherein the alignment portion is configured to line up with the particular alignment subject in a longitudinal direction of the endoscope in a state where the endoscope inserted into the opening and the guide sheath are arranged to have a particular positional relationship in a circumferential direction about a longitudinal axis of the endoscope.

Yet another aspect of the present invention provides a method for attaching a guide sheath to an endoscope by using a positioning aid, the method including: attaching a guide sheath to a distal end portion of an endoscope; attaching the positioning aid to the guide sheath; positioning the guide sheath in a longitudinal direction of the endoscope relative to the endoscope by inserting a distal end surface of the endoscope into the positioning aid up to a particular longitudinal position of the positioning aid; positioning the endoscope at a particular circumferential position of the positioning aid by rotating the endoscope or the guide sheath; and detaching the positioning aid from the guide sheath.

DESCRIPTION OF EMBODIMENTS

A positioning aid 1, a positioning aid system for an endoscope and a guide sheath, and a method for attaching a guide sheath 20 to an endoscope 10 by using the positioning aid 1 according to one embodiment of the present invention will now be described with reference to the drawings.

Figure 1:
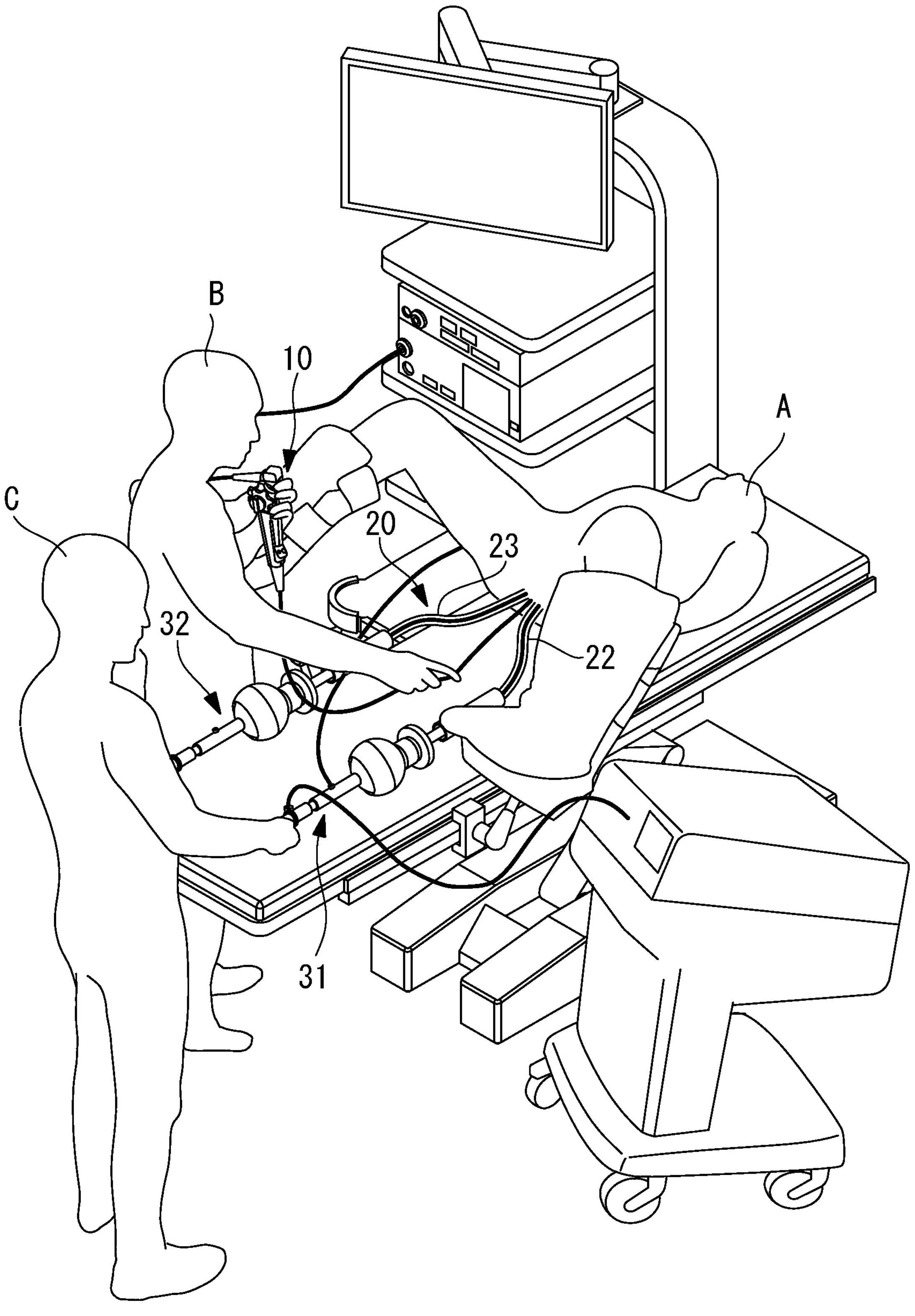
FIG. 1 is a diagram illustrating one example of a surgical procedure in which a medical manipulator system according to one embodiment of the present invention is used.

FIG. 1 illustrates one example of a surgical procedure in which a medical manipulator system equipped with two treatment tools 31 and 32 and the guide sheath 20 is used. The guide sheath 20 is externally attached to a distal end portion of the endoscope 10 and is inserted, together with the endoscope 10, from anus into the body of a patient A lying on a surgical bed. The endoscope 10 is manipulated by a scopist B, and the guide sheath 20 and the treatment tools 31 and 32 are manipulated by a doctor C. The positioning aid 1 according to the present embodiment is used in attaching the guide sheath 20 to a distal end portion of the endoscope 10, and helps position the guide sheath 20 relative to the endoscope 10.

Figure 2A:
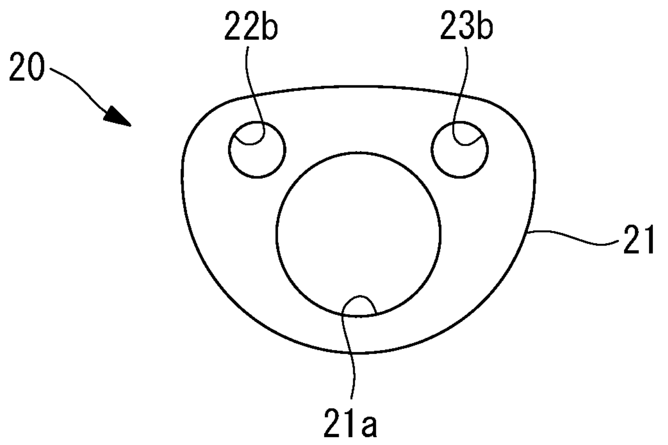
FIG. 2A is a front view of a guide sheath of the medical manipulator system illustrated in FIG. 1.
Figure 2B:
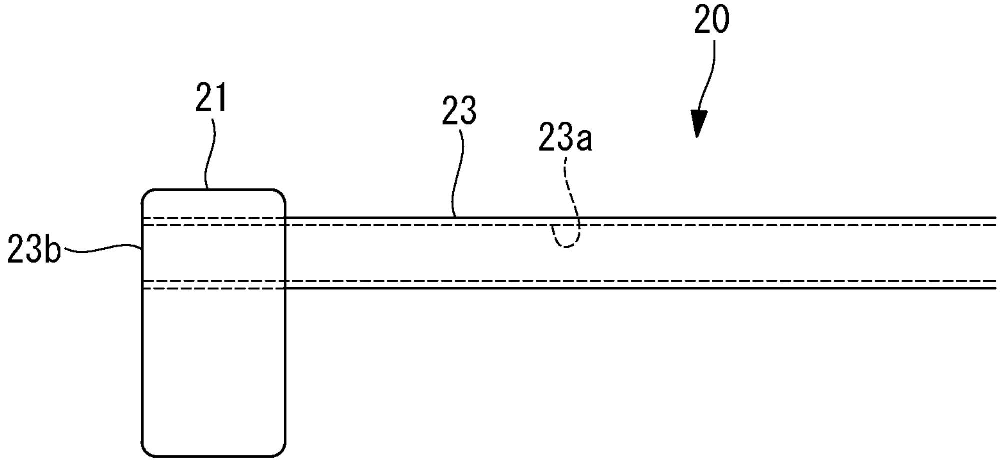
FIG. 2B is a right side view of a distal end portion of the guide sheath illustrated in FIG. 2A.

The positioning aid system is equipped with the guide sheath 20 illustrated in FIGS. 2A and 2B, and the positioning aid 1 illustrated in FIGS. 3A to 3J. The present disclosure also relates to an ornamental design of the positioning aid 1 illustrated in FIGS. 3A to 3J.

Figure 5A:
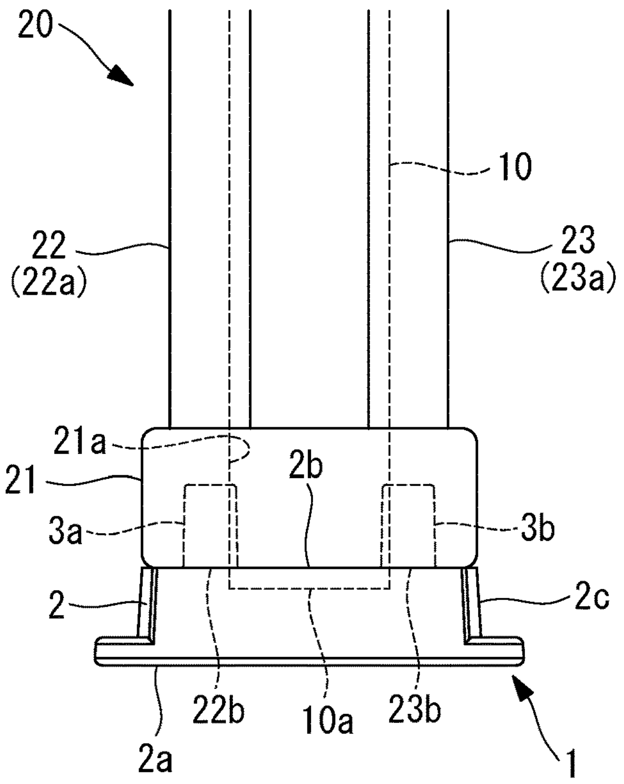
FIG. 5A is a plan view illustrating a state in which the positioning aid illustrated in FIG. 3A is used.

As illustrated in FIGS. 2A, 2B, and 5A, the guide sheath 20 includes an attachment portion 21 to be attached to an outer circumferential surface of a distal end portion of the endoscope 10, and two long flexible tubular sheaths 22 and 23 respectively having treatment tool channels 22*a* and 23*a*.

The attachment portion 21 is a ring-shaped flat member and has an opening 21*a* which penetrates the attachment portion 21 in the thickness direction of the attachment portion 21 and into which the distal end portion of the endoscope 10 is to be inserted. The inner diameter of the opening 21*a* is substantially the same as the outer diameter of the distal end portion of the endoscope 10, and friction between the inner circumferential surface of the attachment portion 21 and the outer circumferential surface of the distal end portion of the endoscope 10 fixes the attachment portion 21 to the distal end portion of the endoscope 10.

Distal end portions of the two sheaths 22 and 23 are fixed to the attachment portion 21, and the two sheaths 22 and 23 extend toward the side opposite the distal end surface of the attachment portion 21. The treatment tool channels 22*a* and 23*a* respectively penetrate through the sheaths 22 and 23 from proximal end surfaces of the sheaths 22 and 23 to the distal end surface of the attachment portion 21, and treatment tools 31 and 32 can be inserted into the treatment tool channels 22*a* and 23*a*. The proximal end portions of the sheaths 22 and 23 may each be equipped with a rigid sheath (see FIG. 8).

Figure 4A:
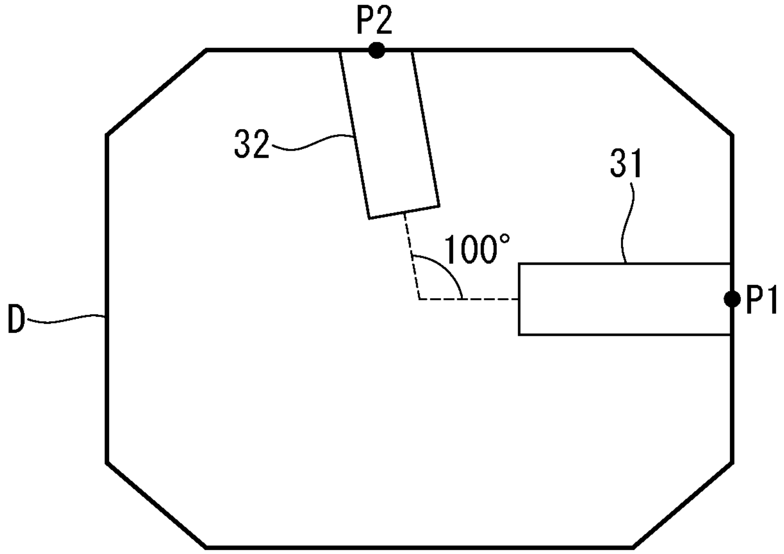
FIG. 4A is a diagram illustrating one example of an endoscopic image that shows the arrangement of two treatment tools.

In the distal end surface of the attachment portion 21, distal end openings 22*b* and 23*b* of the two treatment tool channels 22*a* and 23*a* are located on the radially outer side of the opening 21*a*, and are apart from each other by 100° in the circumferential direction about the center axis of the opening 21*a*. Thus, appearance positions P1 and P2 where the two treatment tools 31 and 32 projecting from the two distal end openings 22*b* and 23*b* appear on an endoscopic image D are as illustrated in FIG. 4A. In other words, the two appearance positions P1 and P2 are apart from each other in the circumferential direction by 100° about the center of the endoscopic image D, and two treatment tools 31 and 32 appear from the two appearance positions P1 and P2 toward the center of the endoscopic image D.

The angle between the two distal end openings 22*b* and 23*b* is not limited to 100°, and can be changed as appropriate depending on the types of the treatment tools 31 and 32, the type of surgical procedure, etc.

As illustrated in FIGS. 3A to 3G, the positioning aid 1 is equipped with a body 2 to be placed at the front of the distal end surface of the endoscope 10 and two attachment portions 3*a* and 3*b* that are used to attach the body 2 to the guide sheath 20 attached to the distal end portion of the endoscope 10.

The body 2 is a flat member that has a front surface 2*a*, a rear surface 2*b*, and a side surface 2*c*. In other words, the front surface 2*a* and the rear surface 2*b* are flat surfaces that face each other in the thickness direction of the body 2 and that are parallel to each other. The side surface 2*c* is a ring-shaped surface that extends along the edges of the front surface 2*a* and the rear surface 2*b*. The body 2 has an opening 4 that penetrates the body 2 in the thickness direction and three abutting portions 5*a*, 5*b*, and 5*c* that project from the inner circumferential surface of the opening 4.

Figure 5B:
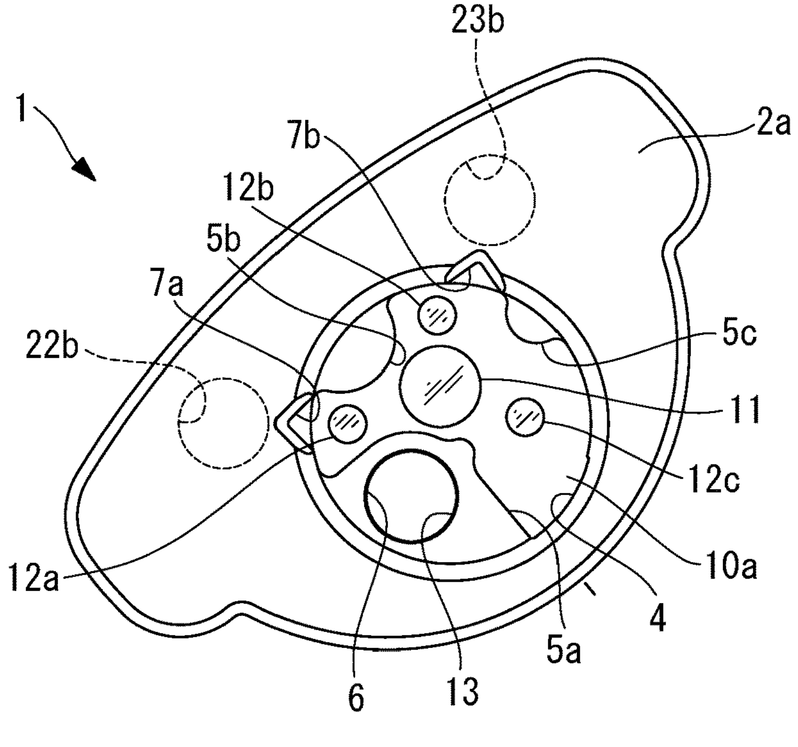
FIG. 5B is a front view illustrating a state in which the positioning aid illustrated in FIG. 3A is used.

The opening 4 has a shape of a cylinder that has a diameter substantially the same as the diameter of the distal end surface 10*a* of the endoscope 10. As illustrated in FIG. 5B, in a state where the body 2 is attached to the guide sheath 20, the opening 4 at the front of the distal end surface 10*a* extends in the longitudinal direction of the endoscope 10, and can accommodate the distal end surface 10*a*. The operator can observe the distal end surface of the endoscope 10 exposed through the opening 4.

Figure 3A:
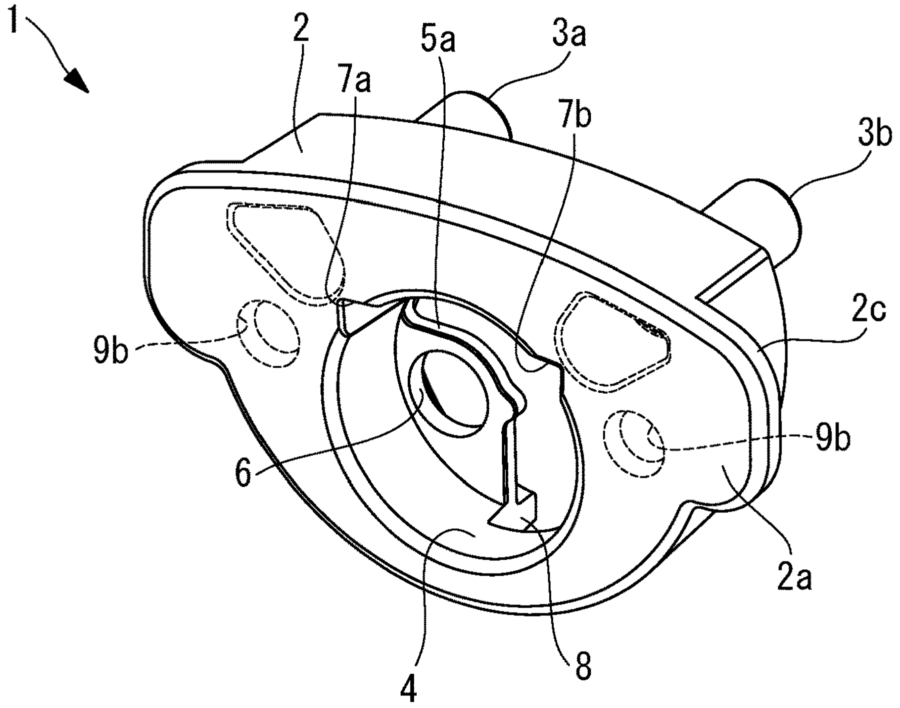
FIG. 3A is a perspective view of a positioning aid according to one embodiment of the present invention.
Figure 3B:
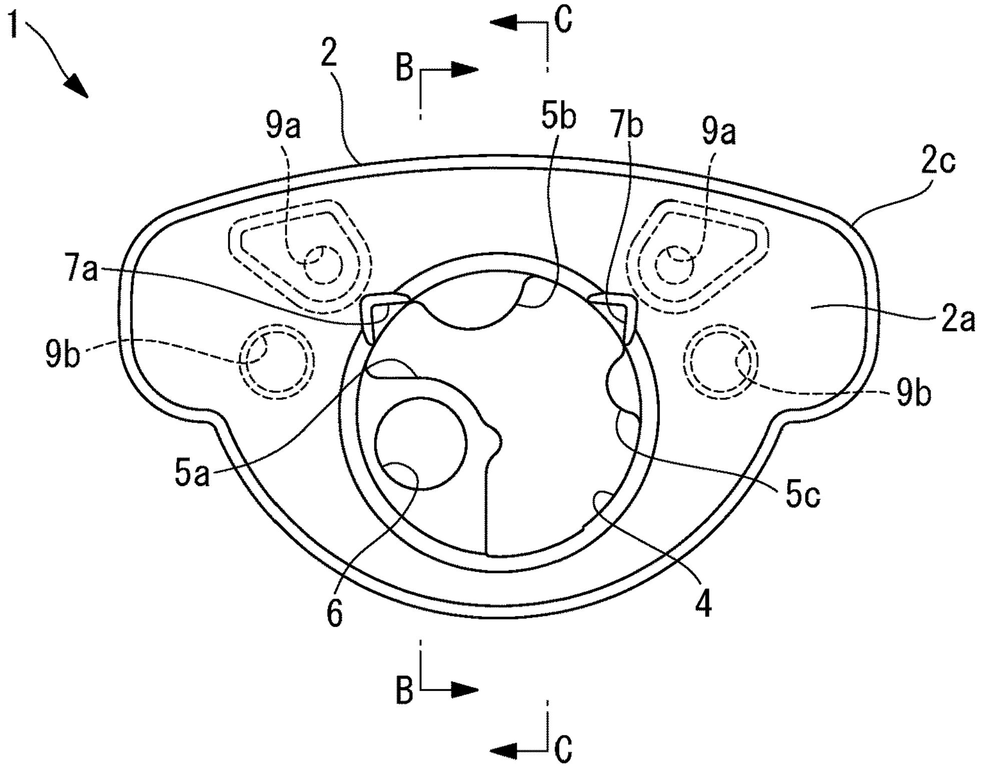
FIG. 3B is a front view of the positioning aid illustrated in FIG. 3A.
Figure 3C:
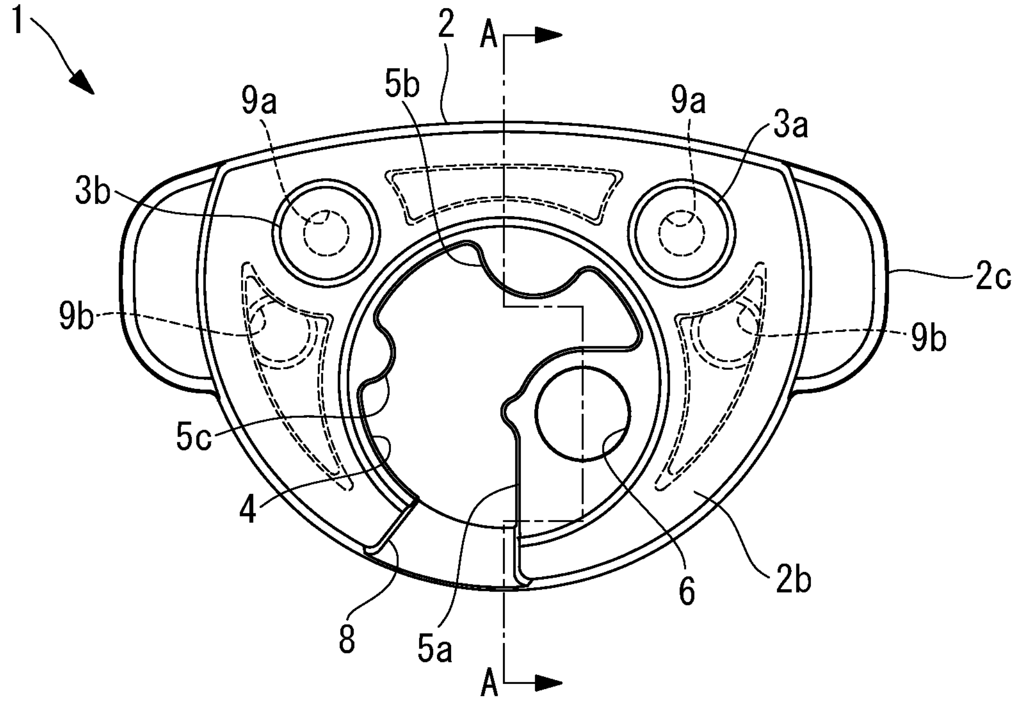
FIG. 3C is a rear view of the positioning aid illustrated in FIG. 3A.
Figure 3D:
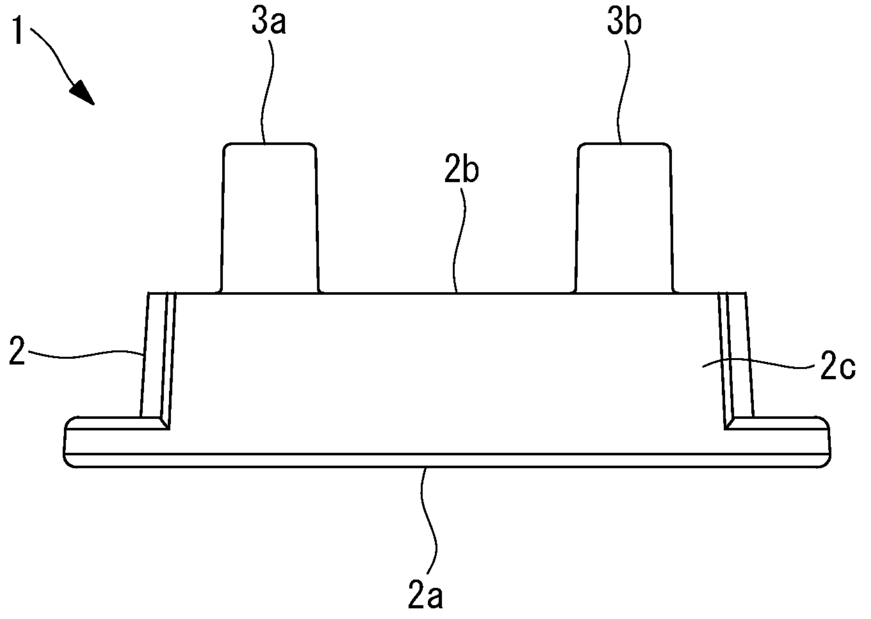
FIG. 3D is a plan view of the positioning aid illustrated in FIG. 3A.
Figure 3E:
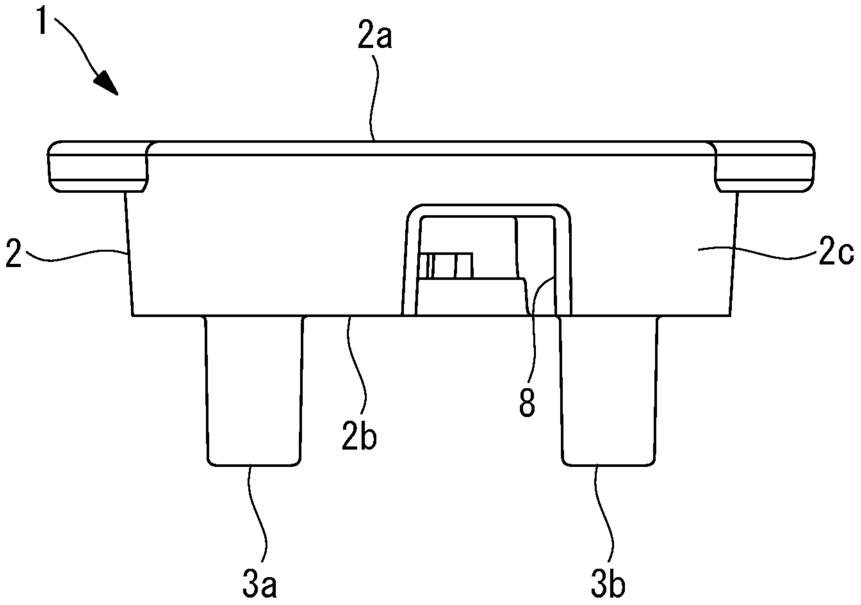
FIG. 3E is a bottom view of the positioning aid illustrated in FIG. 3A.
Figure 3F:
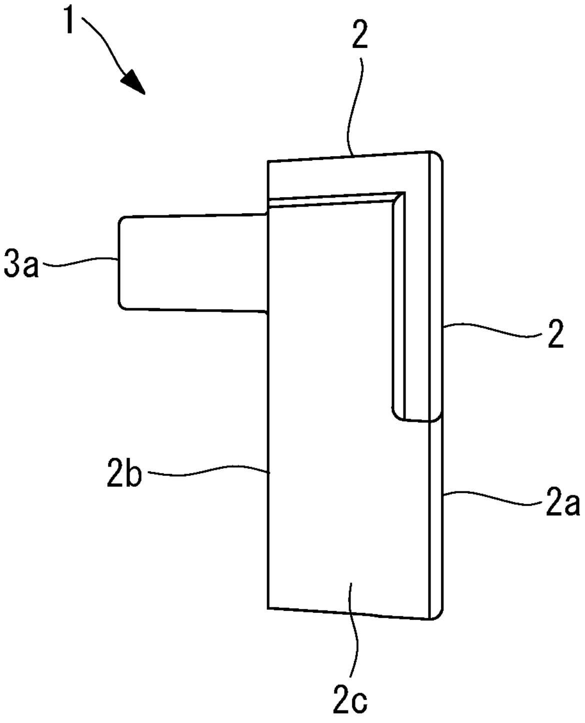
FIG. 3F is a left side view of the positioning aid illustrated in FIG. 3A.
Figure 3G:
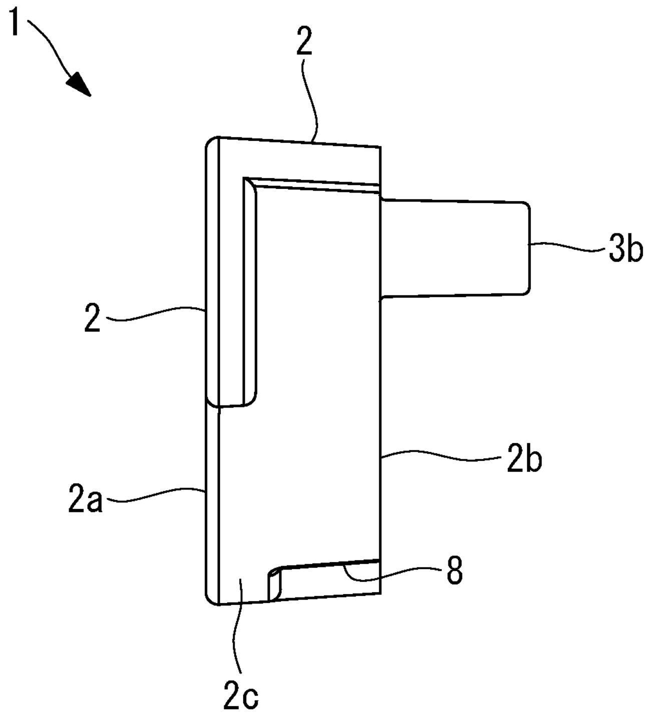
FIG. 3G is a right side view of the positioning aid illustrated in FIG. 3A.
Figure 3H:
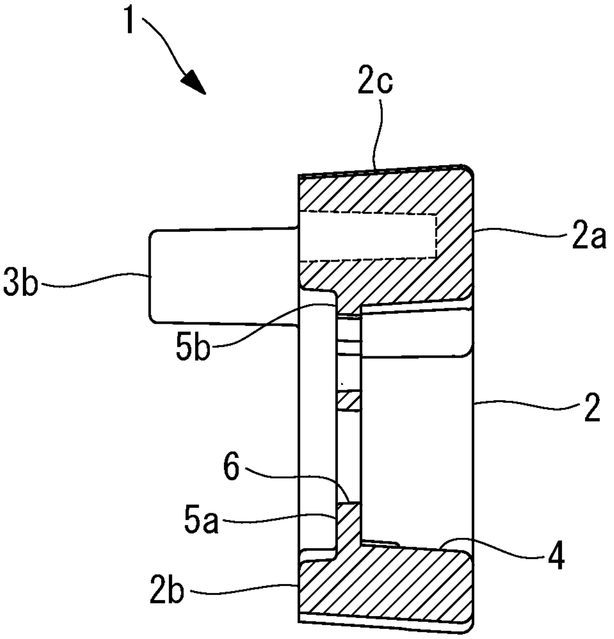
FIG. 3H is a cross-sectional view of the positioning aid illustrated in FIG. 3B taken along line B-B.
Figure 3I:
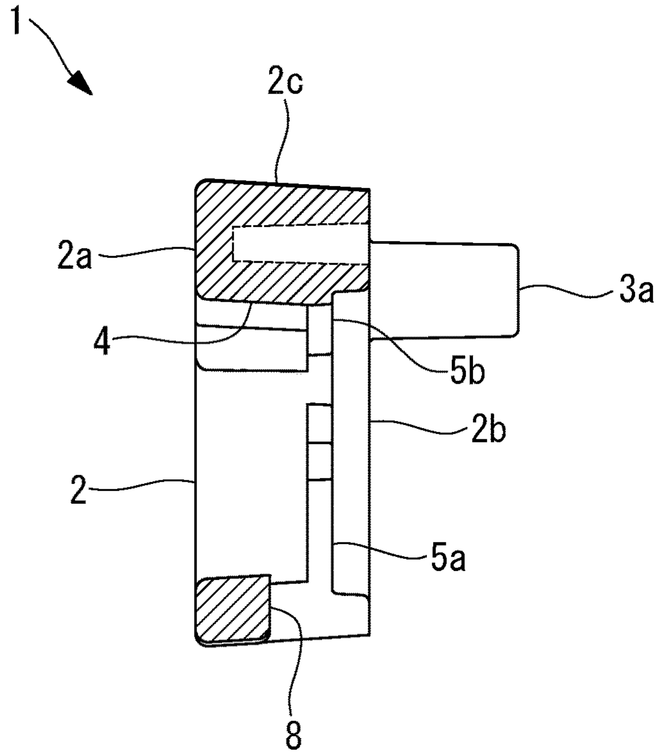
FIG. 3I is a cross-sectional view of the positioning aid illustrated in FIG. 3B taken along line C-C.
Figure 3J:
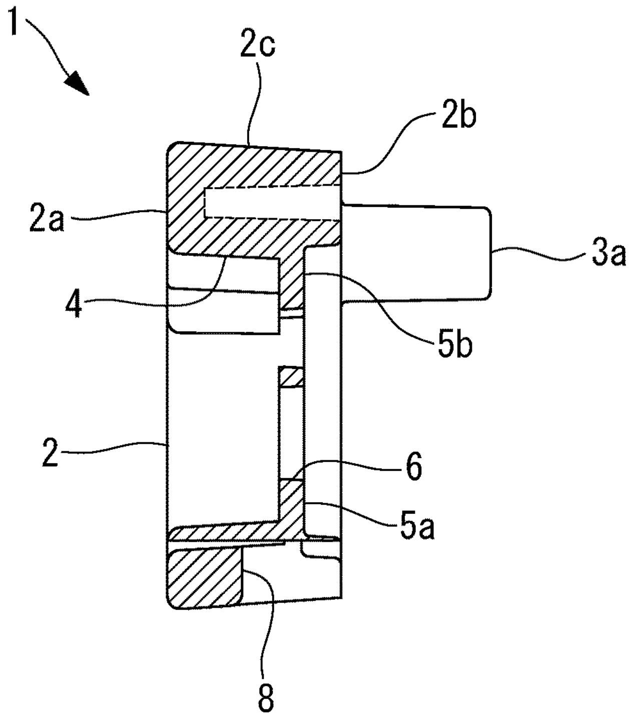
FIG. 3J is a cross-sectional view of the positioning aid illustrated in FIG. 3C taken along line A-A.

As illustrated in FIGS. 3H to 3J, the abutting portions 5*a*, 5*b*, and 5*c* are thin plate-shaped members that extend, from the inner circumferential surface of the opening 4, parallel to the rear surface 2*b*. The three abutting portions 5*a*, 5*b*, and 5*c* are at positions spaced from the rear surface (proximal end surface) 2*b* by the same distance as one another toward the front surface 2*a*, and the distal end surface 10*a* of the endoscope 10 inserted into the opening 4 abuts with the abutting portions 5*a*, 5*b*, and 5*c*.

The three abutting portions 5*a*, 5*b*, and 5*c* are at positions different from one another in the circumferential direction about the center axis of the opening 4. As the distal end surface 10*a* abuts with the three abutting portions 5*a*, 5*b*, and 5*c*, the distal end surface 10*a* can be positioned to be parallel to the rear surface 2*b* and to the distal end surface of the attachment portion 21 abutting with the rear surface 2*b*.

The two attachment portions 3*a* and 3*b* are cylindrical members that project from the rear surface 2*b* of the body 2 in the thickness direction. The two attachment portions 3*a* and 3*b* are at the positions corresponding to the two distal end openings 22*b* and 23*b*, and can be inserted into the two treatment tool channels 22*a* and 23*a*. In other words, in the rear surface 2*b* of the body 2, the two attachment portions 3*a* and 3*b* are located on the radially outer side of the opening 4, and the radial distance from the center axis of the opening 4 to each of the attachment portions 3*a* and 3*b* is equal to the radial distance from the center axis of the opening 21*a* to each of the distal end openings 22*b* and 23*b*. Furthermore, the two attachment portions 3*a* and 3*b* are apart from each other by 100° in the circumferential direction about the center axis of the opening 4. Thus, when the two attachment portions 3*a* and 3*b* are inserted from the two distal end openings 22*b* and 23*b* into the two treatment tool channels 22*a* and 23*a*, the positioning aid 1 becomes attached to the attachment portion 21 while assuming a particular orientation in the circumferential direction about the center axis of the opening 4 such that the opening 4 is positioned to be coaxial with the opening 21*a*.

The body 2 is further equipped with an alignment window 6 formed in the abutting portion 5*a*, two cutouts 7*a* and 7*b* formed in the inner circumferential surface of the opening 4, and an access window 8 formed in the body 2.

The alignment window 6 is provided to position the guide sheath 20 relative to the endoscope 10 so that the guide sheath 20 is at a particular circumferential position about the longitudinal axis of the endoscope 10. The alignment window 6 is formed in only one of the three abutting portions 5*a*, 5*b*, and 5*c*, and is a hole that penetrates through the abutting portion 5*a* in the thickness direction of the abutting portion 5*a*.

Parts such as an objective lens 11 and lighting lenses 12*a*, 12*b*, and 12*c* are installed on the distal end surface 10*a* of the endoscope 10. In addition, a forceps exit 13, which is a distal end opening of a forceps hole penetrating the endoscope 10 in the longitudinal direction, is formed in the distal end surface 10*a* of the endoscope 10.

As illustrated in FIG. 5B, the alignment window 6 is positioned such that, when the guide sheath 20 having the body 2 attached thereto and the endoscope 10 inserted into the opening 4 are arranged to have a particular positional relationship in the circumferential direction of the endoscope 10, the alignment window 6 lines up with the forceps exit 13 in the longitudinal direction of the endoscope 10. The particular positional relationship refers to circumferential positions where, when the distal end surface of the endoscope 10 is viewed from the front, the two distal end openings 22*b* and 23*b* are above and on the left of the objective lens 11. In FIG. 5B, the left, right, top, and bottom of the objective lens 11 are coincident with the left, right, top, and bottom of the plane of the drawing.

The operator observes, from the front, the positioning aid 1 attached to the distal end portion of the endoscope 10 with the attachment portion 21 therebetween, rotates the guide sheath 20 and the positioning aid 1 together relative to the distal end portion of the endoscope 10, and aligns the alignment window 6 with the forceps exit 13 such that the alignment window 6 lines up with the forceps exit 13 in the longitudinal direction of the endoscope 10. As a result, the guide sheath 20 with the positioning aid 1 attached thereto can be positioned at a particular circumferential position relative to the endoscope 10. In order to improve accuracy of aligning the alignment window 6 with the forceps exit 13, the alignment window 6 may have a round shape with a diameter substantially the same as the diameter of the forceps exit 13.

As illustrated in FIG. 5B, the three abutting portions 5*a*, 5*b*, and 5*c* are at positions that do not interfere with the parts 11, 12*a*, 12*b*, and 12*c* on the distal end surface 10*a* in a state where the alignment window 6 is aligned with the forceps exit 13.

Figure 4B:
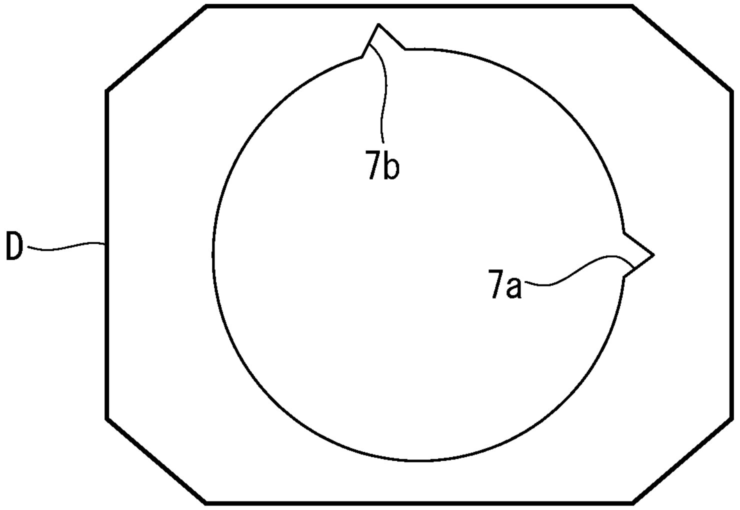
FIG. 4B is a diagram illustrating one example of an endoscopic image that shows the arrangement of two cutouts.

The cutouts 7*a* and 7*b* are formed to extend radially outward from the inner circumferential surface of the opening 4. The cutouts 7*a* and 7*b* are on the distal end side with respect of the abutting portions 5*a*, 5*b*, and 5*c* and are within a viewing area of the endoscope 10 having the distal end surface 10*a* abutting with the abutting portions 5*a*, 5*b*, and 5*c*. The two cutouts 7*a* and 7*b* are at the same positions as the two distal end openings 22*b* and 23*b* in the circumferential direction about the center axis of the opening 4. Accordingly, as illustrated in FIG. 4B, in the endoscopic image D in a state in which the positioning aid 1 is attached to the distal end portion of the endoscope 10 with the guide sheath 20 therebetween, the cutouts 7*a* and 7*b* are observed at the same positions as the appearance positions P1 and P2 in the circumferential direction about the center of the endoscopic image D.

The access window 8 is provided to allow the operator to observe the abutting portions 5*a*, 5*b*, and 5*c* and the distal end surface 10*a* within the opening 4. The access window 8 extends from the rear surface 2*b* and passes through the positions of the abutting portions 5*a*, 5*b*, and 5*c* toward the front surface 2*a* side, and penetrates from the side surface 2*c* of the body 2 to the opening 4. In order to facilitate observation of the abutting portions 5*a*, 5*b*, and 5*c* through the access window 8, the access window 8 is preferably at a position facing at least one abutting portion 5*b* in the radial direction of the opening 4. The operator observes the inside of the opening 4 through the access window 8 so as to confirm whether or not the distal end surface 10*a* of the endoscope 10 abuts with the abutting portions 5*a*, 5*b*, and 5*c*.

As indicated by broken lines in FIGS. 3B and 3C, the positioning aid 1 may have holes 9*a* that penetrate from the rear surfaces of the attachment portions 3*a* and 3*b* to the front surface 2*a*. In a state where the attachment portions 3*a* and 3*b* are inserted into the treatment tool channels 22*a* and 23*a*, the interiors of the treatment tool channels 22*a* and 23*a* communicate with the exterior through the holes 9*a*. Thus, in a state where the positioning aid 1 is attached to the attachment portion 21, a fluid can be fed from the proximal end into the interiors of the treatment tool channels 22*a* and 23*a*. For example, a sterilizing gas may be fed to sterilize the interiors of the treatment tool channels 22*a* and 23*a*.

Furthermore, the positioning aid 1 may have a structure formed due to the method for producing the positioning aid 1. For example, as indicated by broken lines in FIGS. 3A and 3B, holes 9*b* may be formed in the distal end surface of the body 2, and recessed portions may be formed around the holes 9*a*. In addition, as indicated by broken lines in FIG. 3C, one or more than one holes may be formed in the rear surface 2*b*.

Next, a method for manipulating the endoscope 10 and the guide sheath 20 by using the positioning aid 1 is described.

Figure 6:
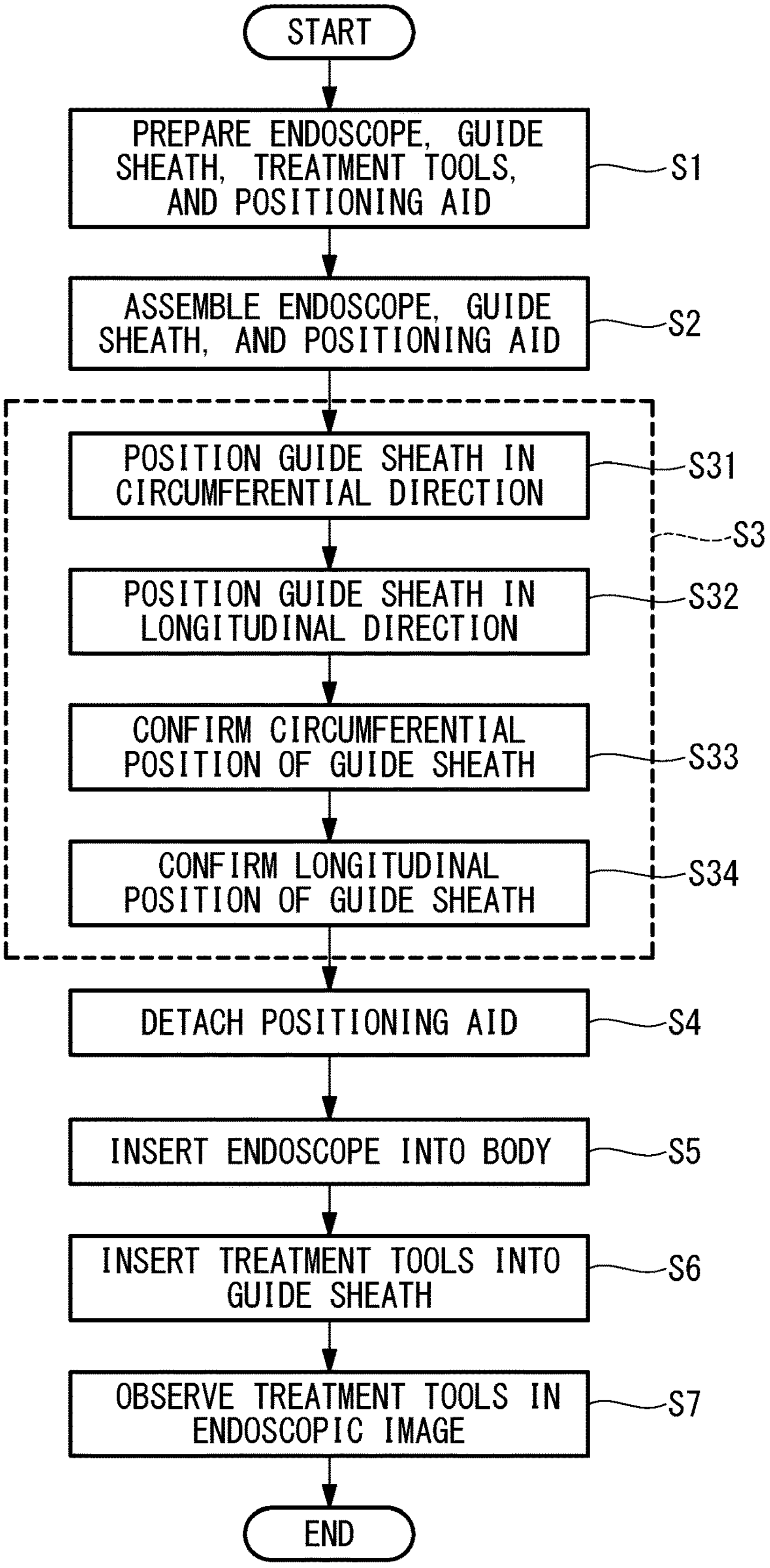
FIG. 6 is a flowchart illustrating a method for manipulating an endoscope and a guide sheath by using the positioning aid illustrated in FIG. 3A.

As illustrated in FIG. 6, a method for manipulating the endoscope 10 and the guide sheath 20 according to the present embodiment includes steps S1 to S6. The method for attaching the guide sheath 20 according to the present embodiment corresponds to steps S1 to S4. The steps S1 to S4 are conducted by any operator, for example, a preparation staff member who is neither the scopist B nor the doctor C.

In the step (first step) S1, the operator prepares the endoscope 10, the guide sheath 20, the treatment tools 31 and 32, and the positioning aid 1.

Next, in step (second step) S2, the operator assembles the endoscope 10, the guide sheath 20, and the positioning aid 2. Specifically, the operator fits the distal end portion of the endoscope 10 into the interior of the attachment portion 21 of the guide sheath 20 so as to attach the guide sheath 20 to the distal end portion of the endoscope 10, and fits the two attachment portions 3*a* and 3*b* into the interiors of the two treatment tool channels 22*a* and 23*a* of the guide sheath 20 so as to attach the positioning aid 1 to the distal end surface of the guide sheath 20.

Next, in step S3, the operator uses the positioning aid 1 to position the guide sheath 20 relative to the endoscope 10.

Step S3 includes a step (fourth step) S31 of positioning the guide sheath 20 to a particular circumferential position relative to the endoscope 10, a step (third step) S32 of positioning the guide sheath 20 at a particular longitudinal position relative to the endoscope 10, a step (sixth step) S33 of confirming the circumferential position of the guide sheath 20 relative to the endoscope 10 on the basis of the endoscopic image D, and a step S34 of confirming the longitudinal position of the guide sheath 20 relative to the endoscope 10 by using the access window 8.

In the step S31, the operator observes the positioning aid 1 from the front and relatively rotates the positioning aid 1 attached to the guide sheath 20 and the endoscope 10 up to a particular circumferential position where the alignment window 6 is in line with the forceps exit 13. As a result, the guide sheath 20 is positioned at a particular circumferential position relative to the endoscope 10.

In step S32, the operator relatively moves the positioning aid 1 attached to the guide sheath 20 and the endoscope 10 in the longitudinal direction of the endoscope 10, and inserts the distal end surface 10*a* into the opening 4 up to a particular longitudinal position where the distal end surface 10*a* abuts with the abutting portions 5*a*, 5*b*, and 5*c*. As a result, the guide sheath 20 is positioned at a particular longitudinal position relative to the endoscope 10.

Step S31 and step S32 may be performed in any order. In other words, step S31 may be performed before or after step S32.

After step S31, in step S33, the operator actuates the endoscope 10 and causes an endoscopic image D acquired by the endoscope 10 to be displayed on a monitor. The operator confirms that the two cutouts 7*a* and 7*b* in the endoscopic image D are positioned on the right side and the upper side within the endoscopic image D. If the two cutouts 7*a* and 7*b* are not on the right side and the upper side within the endoscopic image D, the operator corrects the circumferential positions of the guide sheath 20 and the positioning aid 1 relative to the endoscope 10 while observing the endoscopic image D.

After step S32, in step S34, the operator observes the endoscope 10 within the opening 4 through the access window 8 to confirm that the distal end surface 10*a* projects from the distal end surface of the attachment portion 21 and abuts with the abutting portions 5*a*, 5*b*, and 5*c*. If the distal end surface 10*a* is not appropriately abutting with the abutting portions 5*a*, 5*b*, and 5*c*, the operator corrects the position of the distal end surface 10*a* while observing the interior of the opening 4 through the access window 8.

The order in which step S33 and step S34 are performed may be any. In other words, step S33 may be performed before or after step S34.

Next, in step (fifth step) S4, the operator detaches the positioning aid 1 from the guide sheath 20.

Next, in step S5, the scopist B inserts the endoscope 10 with the guide sheath 20 attached thereto into the body of the patient A.

Next, in step S6, the doctor C inserts the treatment tools 31 and 32 into the treatment tool channels 22*a* and 23*a* of the guide sheath 20. The distal end portions of the treatment tools 31 and 32 projecting from the distal end openings 22*b* and 23*b* in the body of the patient A are within the viewing area of the endoscope 10 and appear in the endoscopic image D.

Next, in the step S7, the doctor C observes the endoscopic image D that includes the two treatment tools 31 and 32. The two treatment tools 31 and 32 appear from the two appearance positions P1 and P2 on the right side and the upper side as with the cutouts 7*a* and 7*b* confirmed in step S33. The doctor C can treat tissue in the living body by manipulating the two treatment tools 31 and 32 while observing the endoscopic image D.

In step S7, the two treatment tools 31 and 32 are preferably arranged at particular positions in particular directions in the endoscopic image D. For example, when the treatment tool 31 is a surgical knife and the treatment tool 32 is forceps, the surgical knife 31 preferably projects from the appearance position P1 near the center on the right side of the endoscopic image D, and the forceps 32 preferably project from the appearance position P2 near the center of the upper side of the endoscopic image D.

However, when the relative positions of the objective lens 11 on the distal end surface 10*a* and the two distal end openings 22*b* and 23*b* of the guide sheath 20 are aligned by eye only, the alignment may become inaccurate and may vary from operator to operator, which makes it difficult to accurately position the guide sheath 20 relative to the endoscope 10 so that the distal end openings 22*b* and 23*b* are appropriately placed relative to the objective lens 11.

According to the present embodiment, the guide sheath 20 can be reliably attached to a particular attachment position relative to the endoscope 10 by using the positioning aid 1 irrespective of who attached the guide sheath 20 to the endoscope 10. In other words, the guide sheath 20 can be attached to a particular circumferential position relative to the endoscope 10 so that the appearance positions P1 and P2 of the treatment tools 31 and 32 are particular positions within the endoscopic image D. Furthermore, the guide sheath 20 can be attached to a particular longitudinal position relative to the endoscope 10 so that the distal end surface 10*a* of the endoscope 10 projects from the distal end surface of the attachment portion 21 by a particular amount.

In addition, the alignment portion constituted by the alignment window 6 is visually aligned in a non-contact manner with the forceps exit 13 which is an alignment subject. Thus, the alignment portion can be prevented from coming into contact with the parts on the distal end surface 10*a* of the endoscope 10, for example.

Furthermore, the circumferential position of the guide sheath 20 relative to the endoscope 10 is adjusted by using the alignment window 6 by visual observation from the outer side of the endoscope 10 in the step S31, and then confirmed through the endoscopic image D by using the cutouts 7*a* and 7*b* in the step S33. As described above, the guide sheath 20 can be more reliably attached to a particular circumferential position by confirming the circumferential position of the guide sheath 20 relative to the endoscope 10 from two different points of view.

In particular, step S31 is preferably performed by a first operator, and step S33 is preferably performed by a second operator who is different from the first operator. For example, step S31 may be performed by a preparation staff member (first operator) and step S33 may be performed by the doctor C (second operator). In this manner, the circumferential position of the guide sheath 20 can be double-checked by two operators.

Figure 7:
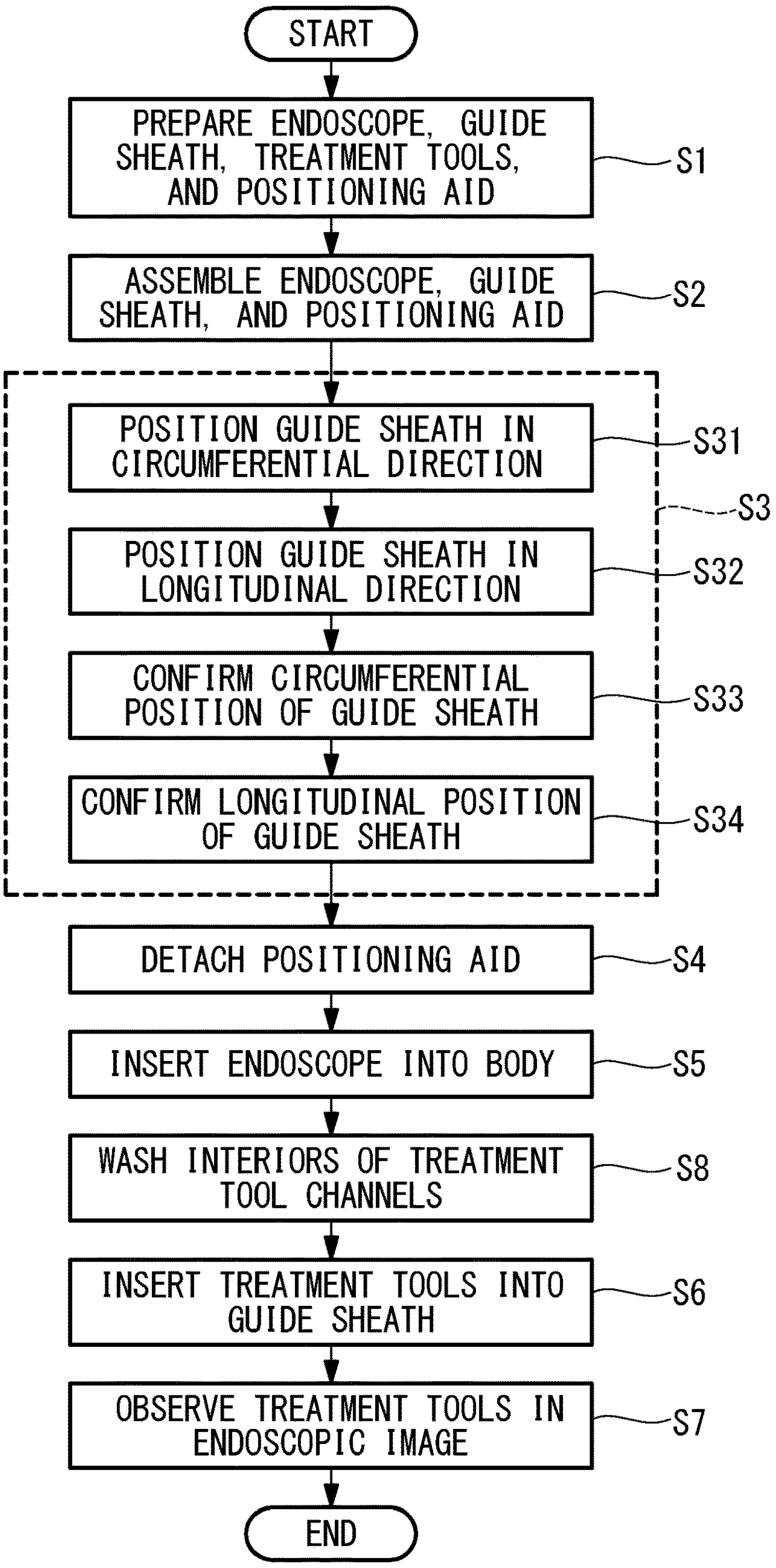
FIG. 7 is a flowchart illustrating a modification of a method for manipulating an endoscope and a guide sheath by using the positioning aid illustrated in FIG. 3A.

During the process of inserting the guide sheath 20 into the body in the step S7, foreign matter such as body tissue may enter the interiors of the treatment tool channels 22*a* and 23*a* and clog the interiors of the treatment tool channels 22*a* and 23*a*. Thus, as illustrated in FIG. 7, a step S8 of washing the interiors of the treatment tool channels 22*a* and 23*a* by letting washing water flow through the treatment tool channels 22*a* and 23*a* may be added between the step S5 and the step S6.

Figure 8:
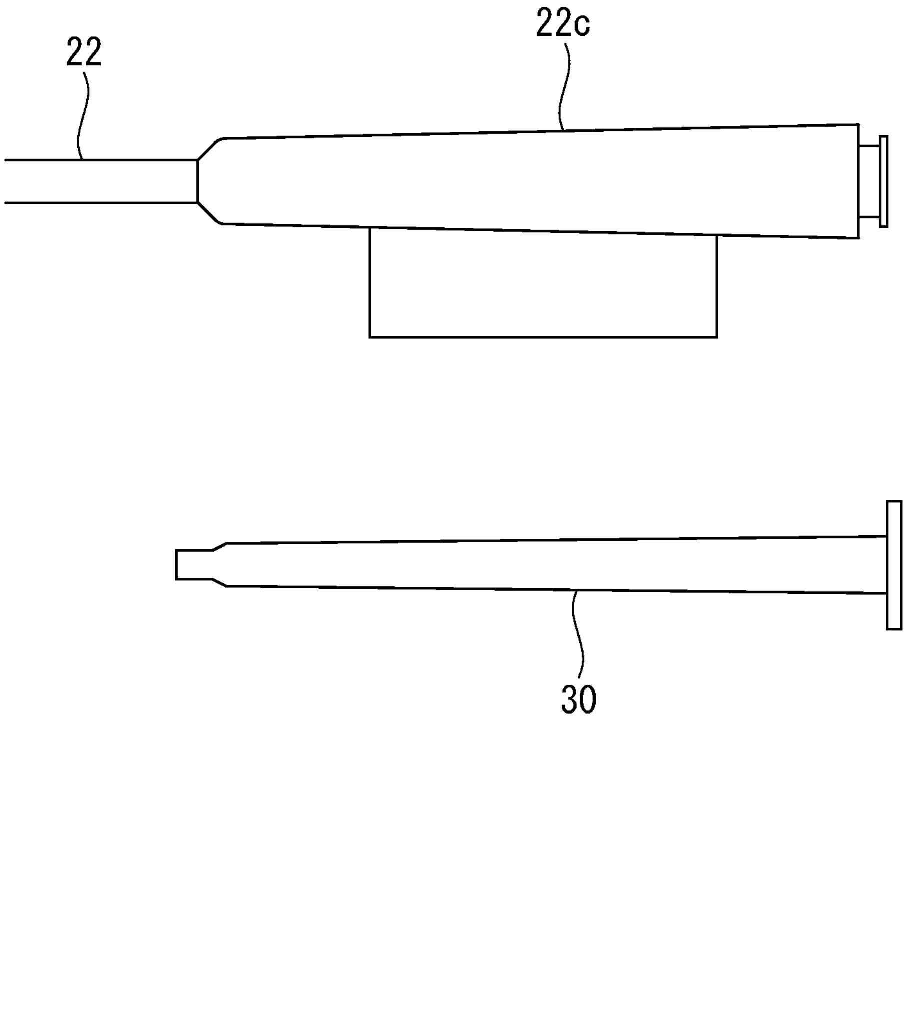
FIG. 8 is a diagram illustrating one example of a jet unit used to supply a washing liquid.

In the step S8, a jet unit 30 inserted into the rigid sheath of each of the sheaths 22 and 23 may be used to increase the water pressure of the washing liquid. FIG. 8 illustrates one example of the jet unit 30. The jet unit 30 is an accessory component of the guide sheath 20 and is a tubular member that has openings at both ends. The outer diameter of the jet unit 30 is smaller than the inner diameter of the rigid sheath 22*c*, and the internal capacity of the jet unit 30 is smaller than the internal capacity of the rigid sheath 22*c*.

In step S8, the jet unit 30 is installed in the rigid sheath 22*c*, a syringe (not illustrated) is connected to the proximal end of the jet unit 30, and the washing liquid is jetted out into the jet unit 30 from the syringe. The washing liquid is fed to the treatment tool channels 22*a* and 23*a* from the jet unit 30, and foreign matter in the treatment tool channels 22*a* and 23*a* is washed away by the washing liquid flowing in the treatment tool channels 22*a* and 23*a* toward the distal end openings 22*b* and 23*b*.

Here, since the internal capacity of the jet unit 30 is smaller than the internal capacity of the rigid sheath 22*c*, the water pressure of the washing liquid supplied to the treatment tool channels 22*a* and 23*a* can be increased compared to when the washing liquid is directly supplied to the rigid sheath 22*c* without using the jet unit 30, and thus the interiors of the treatment tool channels 22*a* and 23*a* can be efficiently washed.

Figure 9:
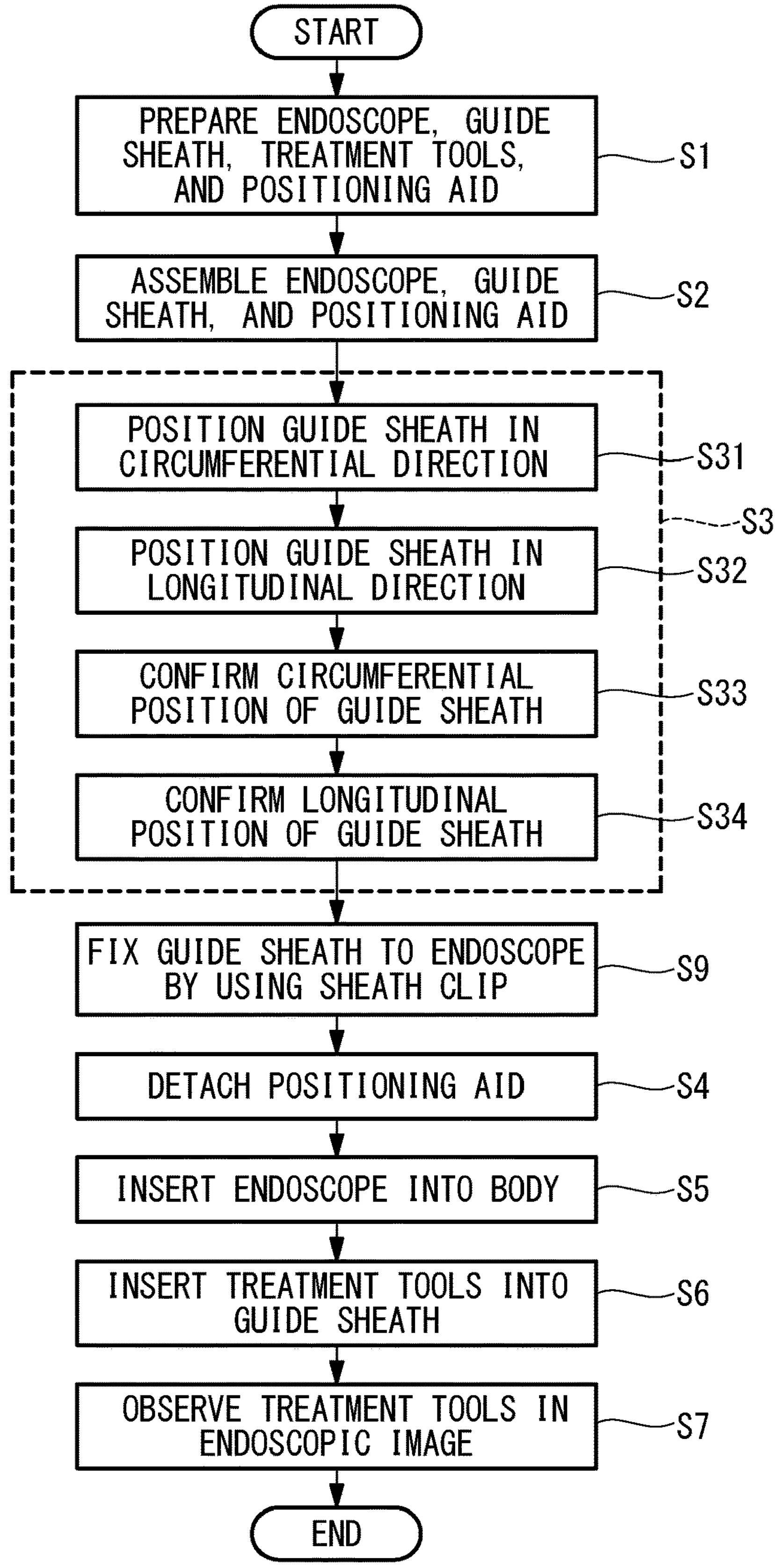
FIG. 9 is a flowchart illustrating another modification of a method for manipulating an endoscope and a guide sheath by using the positioning aid illustrated in FIG. 3A.

In the present embodiment, as illustrated in FIG. 9, a step S9 of fixing the guide sheath 20 to the endoscope 10 by using a sheath clip 40 may be added. The step S9 is performed at any desired timing after the step S3 and before the step S5.

Figure 10:
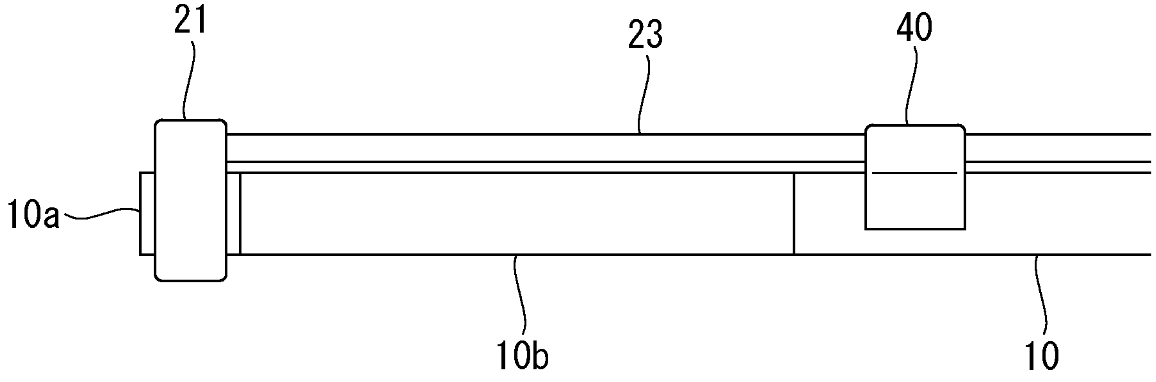
FIG. 10 is a diagram illustrating one example of a sheath clip for fixing a guide sheath to an endoscope.

The sheath clip 40 is an accessory of the guide sheath 20. As illustrated in FIG. 10, the sheath clip 40 fixes the sheaths 22 and 23 onto the endoscope 10 so that the sheaths 22 and 23 are positioned on the proximal end side with respect to a bending portion 10*b* of the endoscope 10. In this manner, the sheaths 22 and 23 are fixed to the endoscope 10 on the distal end side and the proximal end side of the bending portion 10*b* by the attachment portion 21 and the sheath clip 40.

When the sheaths 22 and 23 are fixed to the endoscope 10 by only the attachment portion 21, the sheaths 22 and 23 bend along with the bend of the bending portion 10*b*, and the guide sheath 20 remains bent after the bending portion 10*b* returns to a straight-line shape from a bent shape. The distal end portions of the sheaths 22 and 23 that remain bent within the body can obstruct movements of the guide sheath 20, etc., in the body cavity.

When the sheaths 22 and 23 are fixed by the sheath clip 40 to the endoscope 10 on the proximal end side of the bending portion 10*b* also, the portions that lie between the attachment portion 21 of the sheaths 22 and 23 and the sheath clip 40 undergo deformation between a bent shape and a straight-line shape by following the deformation of the bending portion 10*b*. As a result, the aforementioned issues can be avoided.

In the present embodiment, the alignment window 6 is a circular hole; alternatively, the alignment portion may take any other form. In addition, there are characteristic structures, such as lighting lenses 12*a*, 12*b*, and 12*c*, in addition to the forceps exit 13 on the distal end surface 10*a* of the endoscope 10. The alignment subject may be any characteristic structure other than the forceps exit 13.

Figure 11A:
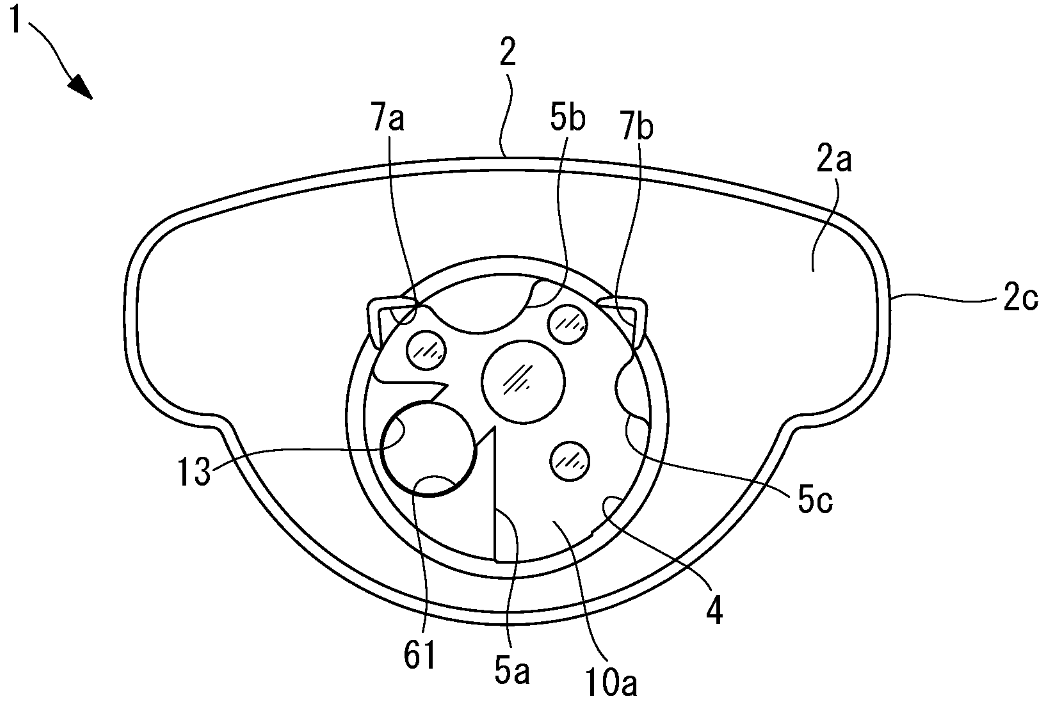
FIG. 11A is a front view of the positioning aid and illustrates another example of an alignment portion.
Figure 11B:
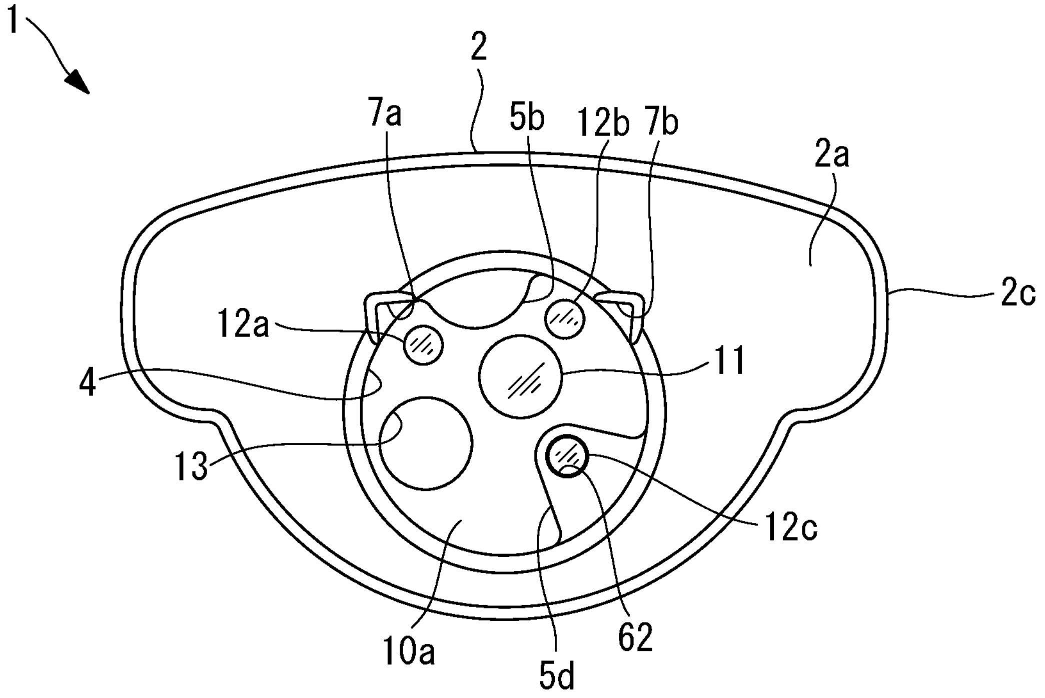
FIG. 11B is a front view of the positioning aid and illustrates yet another example of the alignment portion.

FIGS. 11A and 11B illustrate other examples of the alignment portion and the alignment subject. In FIG. 11A, the abutting portion 5*a* has a letter-C shape that opens toward the radially inner side, and an alignment portion 61 is an alignment window that penetrates the abutting portion 5*a* in the thickness direction and opens toward the radially inner side. As with the alignment portion 6, an alignment portion 62 illustrated in FIG. 11B is a hole in the abutting portion 5*d*, and is at a position corresponding to the lighting lens 12*c* which is the alignment subject.

The alignment portion may be a protrusion that fits with a recess in the distal end surface 10*a* or a recess that fits with a protrusion on the distal end surface 10*a*. For example, the alignment portion may be a protrusion that fits with the interior of the forceps exit 13 (alignment subject) or a recess that fits with the jet nozzle (alignment subject) projecting from the distal end surface 10*a* of the endoscope 10.

According to this structure, engagement between the alignment portion and the alignment subject can mechanically position the guide sheath 20, which has the positioning aid 1 attached thereto, at a particular circumferential position relative to the endoscope 10.

In the present embodiment, the positioning aid 1 has three abutting portions 5*a*, 5*b*, and 5*c*; however, the number of abutting portions can be modified as appropriate as long as the positioning aid 1 has at least one abutting portion.

In the present embodiment, the positioning aid 1 has cutouts 7*a* and 7*b* as the marks indicating the appearance positions P1 and P2 of the treatment tools 31 and 32 in the endoscopic image D; alternatively, the positioning aid 1 may have any other type of marks formed on the inner circumferential surface of the opening 4.

For example, the marks may be graphics such as lines and circles drawn on the inner circumferential surface of the opening 4. Alternatively, the marks may be projections such as triangular and rectangular projections that project radially inward from the inner circumferential surface of the opening 4.

The following aspects can be derived from the embodiments.

An aspect of the present invention provides a positioning aid that can be attached to a guide sheath for inserting an endoscope and that helps position the guide sheath relative to the endoscope, the positioning aid including: an opening that penetrates in a longitudinal direction of the endoscope and into which a distal end portion of the endoscope can be inserted; and an alignment portion to be aligned with a particular alignment subject that is present on a distal end surface of the endoscope, wherein the alignment portion lines up with the particular alignment subject in the longitudinal direction of the endoscope in a state where the endoscope inserted into the opening and the guide sheath are arranged to have a particular positional relationship in a circumferential direction about a longitudinal axis of the endoscope.

According to this aspect, in a state where the positioning aid is attached to the guide sheath attached to the distal end portion of the endoscope, the operator can observe, from the front, the distal end surface of the endoscope through the opening disposed at the front of the distal end surface of the endoscope. The operator can reliably attach the guide sheath to a particular circumferential position relative to the endoscope by relatively rotating the endoscope and the positioning aid attached to the guide sheath in the circumferential direction of the endoscope so that the endoscope and the positioning aid are set at such positions that the alignment portion lines up with the particular alignment subject on the distal end surface of the endoscope in the longitudinal direction of the endoscope.

In the aforementioned aspect, the positioning aid may further include at least one abutting portion that is disposed on an inner side of the opening and that positions the endoscope at a particular position in the longitudinal direction when the distal end surface of the endoscope inserted into the opening abuts with the abutting portion.

According to this feature, the guide sheath can be reliably attached to the particular longitudinal position relative to the endoscope by relatively moving the endoscope and the positioning aid attached to the guide sheath in the longitudinal direction of the endoscope so that the endoscope and the positioning aid are set at such positions that the distal end surface of the endoscope abuts with the abutting portion in the opening.

In the aforementioned aspect, the at least one abutting portion may include a plurality of abutting portions disposed at positions different from one another in a circumferential direction about a center axis of the opening.

According to this feature, the distal end surface of the endoscope can be arranged to have a particular tilt relative to the guide sheath by causing the distal end surface of the endoscope to abut with the plurality of abutting portions simultaneously.

In the aforementioned aspect, the alignment portion may be a window that is formed in one of the abutting portions and that penetrates the abutting portion in a direction parallel to a center axis of the opening.

According to this structure, the alignment portion can be aligned relative to the alignment subject without causing the alignment portion to contact the alignment subject.

In the aforementioned aspect, a mark to be placed within a viewing area of the endoscope having the distal end surface abutting with the abutting portion may be disposed on an inner surface of the opening, and, in a state where the positioning aid is attached to the guide sheath, the mark may be disposed at the same position as a distal end opening of a treatment tool channel of the guide sheath in a circumferential direction about a center axis of the opening.

According to this feature, in a state where the distal end surface of the endoscope is caused to abut with the abutting portion, in the endoscopic image, the mark is observed at the same position as the position where a treatment tool appears in the circumferential direction about the center of the endoscopic image. Thus, after the guide sheath is positioned relative to the endoscope in the circumferential direction by using the alignment portion, the observer can confirm, on the basis of the position of the mark in the endoscopic image, that the guide sheath is positioned at the particular circumferential position relative to the endoscope.

Another aspect of the present invention provides a positioning aid system for an endoscope and a guide sheath, the positioning aid system including a guide sheath into which an endoscope is to be inserted, and the aforementioned positioning aid that can be attached to the guide sheath and that helps position the guide sheath relative to the endoscope.

Yet another aspect of the present invention provides a method for attaching a guide sheath to an endoscope by using a positioning aid, the method including: a first step of preparing the endoscope, the guide sheath, and the positioning aid; a second step of attaching the guide sheath to a distal end portion of the endoscope and attaching the positioning aid to the guide sheath; a third step of inserting a distal end surface of the endoscope into the positioning aid up to a particular longitudinal position of the positioning aid so as to position the guide sheath in a longitudinal direction of the endoscope relative to the endoscope; a fourth step of rotating one of the endoscope and the guide sheath so as to position the endoscope at a particular circumferential position of the positioning aid; and a fifth step of detaching the positioning aid from the guide sheath.

In the aforementioned aspect, the method may further include a sixth step of confirming, on the basis of an endoscopic image acquired by the endoscope, that the endoscope is disposed at the particular circumferential position relative to the positioning aid.

According to this feature, after the fourth step, the operator can confirm, on the basis of the endoscopic image, that the guide sheath is positioned at the particular circumferential position relative to the endoscope.

In the aforementioned aspect, the third step may be performed by a first operator, and the fourth step may be performed by a second operator different from the first operator.

According to this feature, two operators can double-check that the guide sheath is positioned at the particular circumferential position relative to the endoscope.

In the aforementioned aspect, in the third step, the endoscope may be positioned at the particular longitudinal position by causing the distal end surface of the endoscope to abut with an abutting portion of the positioning aid, the abutting portion being disposed on an inner side of an opening that penetrates the positioning aid in the longitudinal direction of the endoscope and into which the distal end portion of the endoscope is inserted; in the fourth step, the endoscope may be positioned at the particular circumferential position by bringing an alignment portion of the positioning aid to be in line with a particular alignment subject on the distal end surface of the endoscope, and, in a state where the endoscope inserted into the opening and the guide sheath are arranged to have a particular positional relationship in a circumferential direction about a longitudinal axis of the endoscope, the alignment portion may line up with the particular alignment subject in the longitudinal direction of the endoscope; and in the sixth step, a position of a mark within the endoscopic image may be confirmed, the mark being disposed at a particular position in a circumferential direction about a center axis of the opening and being disposed on an inner surface of the opening.

REFERENCE SIGNS LIST

1 positioning aid
2 body
3*a*, 3*b* attachment portion
4 opening
5*a*, 5*b*, 5*c* abutting portion
6 alignment window, alignment portion
7*a*, 7*b* cutout
8 access window
10 endoscope
10*a* distal end surface
13 forceps exit (alignment subject)
20 guide sheath
22*a*, 23*a* treatment tool channel
22*b*, 23*b* distal end opening
D endoscopic image
P1, P2 appearance position

The invention claimed is:

1. A positioning aid comprising:
an opening configured to receive a distal end portion of an endoscope,
an abutting surface extending radially inward from an inner surface of the opening, wherein the abutting surface is configured to abut the distal end surface of the endoscope;
a window located on the abutting surface and configured to be aligned with a particular alignment subject on a distal end surface of the endoscope; and multiple second abutting surfaces disposed at different positions from one another in a circumferential direction about a center axis of the opening.

2. The positioning aid according to claim 1, wherein the window penetrates the abutting surface in a direction parallel to a center axis of the opening.

3. The positioning aid according to claim 1, wherein a mark is placed within a viewing area of the endoscope having the distal end surface abutting with the abutting surface, and wherein in a state where the positioning aid is attached to a guide sheath, the mark is disposed at the same position as a distal end opening of a treatment tool channel of the guide sheath in a circumferential direction about a center axis of the opening.

4. The positioning aid according to claim 1, wherein the window is configured to line up with the particular alignment subject in a longitudinal direction of the endoscope in a state where the endoscope inserted into the opening and a guide sheath are arranged to have a particular positional relationship in a circumferential direction about a longitudinal axis of the endoscope.

5. The positioning aid according to claim 1, further comprising:

an attachment member configured to be aligned with a guide sheath, the attachment member being located radially outward from the opening.

6. The positioning aid according to claim 5, wherein the attachment member is a protrusion, and wherein the protrusion is inserted in the guide sheath.

7. A positioning aid system comprising:

a guide sheath configured to receive an endoscope; and a positioning aid configured to be attached to the guide sheath wherein the positioning aid includes:

an opening configured to receive a distal end portion of the endoscope;

an abutting surface extending radially inward from an inner surface of the opening, wherein the abutting surface is configured to abut the distal end surface of the endoscope;

a window located on the abutting surface and configured to be aligned with a particular alignment subject on a distal end surface of the endoscope; and multiple second abutting surfaces disposed at positions different from one another in a circumferential direction about a center axis of the opening.

8. The positioning aid system according to claim 7, wherein the window penetrates the abutting surface in a direction parallel to a center axis of the opening.

9. The positioning aid system according to claim 7, wherein a mark is placed within a viewing area of the endoscope having the distal end surface abutting with the abutting surface, and wherein in a state where the positioning aid is attached to the guide sheath, the mark is disposed at the same position as a distal end opening of a treatment tool channel of the guide sheath in a circumferential direction about a center axis of the opening.

10. The positioning aid system according to claim 7, wherein the window is configured to line up with the particular alignment subject in a longitudinal direction of the endoscope in a state where the endoscope inserted into the opening and the guide sheath are arranged to have a particular positional relationship in a circumferential direction about a longitudinal axis of the endoscope.

11. The positioning aid system according to claim 7, further comprising:

an attachment member configured to be aligned with the guide sheath, the attachment member being located radially outward from the opening.

12. The positioning aid system according to claim 11, wherein the attachment member is a protrusion, and wherein the protrusion is inserted into the guide sheath.

13. A method for attaching a guide sheath to an endoscope by using a positioning aid, the method comprising:

attaching a guide sheath to a distal end portion of an endoscope;

attaching the positioning aid to the guide sheath;

positioning the guide sheath in a longitudinal direction of the endoscope relative to the endoscope by inserting a distal end surface of the endoscope into the positioning aid up to a particular longitudinal position of the positioning aid;

positioning the endoscope at a particular circumferential position of the positioning aid by rotating the endoscope or the guide sheath; and detaching the positioning aid from the guide sheath before inserting the guide sheath and the endoscope into a body.

14. The method for attaching a guide sheath according to claim 13, further comprising:

confirming, based at least in part on an endoscopic image acquired by the endoscope, that the endoscope is disposed at the particular circumferential position relative to the positioning aid.

15. The method for attaching a guide sheath according to claim 14, wherein:

in the inserting, the endoscope is positioned at the particular longitudinal position by causing the distal end surface of the endoscope to abut with an abutting portion of the positioning aid, the abutting portion being disposed on an inner side of an opening that penetrates the positioning aid in the longitudinal direction of the endoscope and into which the distal end portion of the endoscope is inserted;

in the rotating, the endoscope is positioned at the particular circumferential position by bringing an alignment portion of the positioning aid to be in line with a particular alignment subject on the distal end surface of the endoscope, and, in a state where the endoscope inserted into the opening and the guide sheath are arranged to have a particular positional relationship in a circumferential direction about a longitudinal axis of the endoscope, wherein the alignment portion lines up with the particular alignment subject in the longitudinal direction of the endoscope; and in the confirming, a position of a mark within the endoscopic image is confirmed, the mark being disposed at a particular position in a circumferential direction about a center axis of the opening and being disposed on an inner surface of the opening.

* * * * *